United States Patent [19]
Dobak, III

[11] Patent Number: 6,042,559
[45] Date of Patent: Mar. 28, 2000

[54] INSULATED CATHETER FOR SELECTIVE ORGAN PERFUSION

[75] Inventor: John D. Dobak, III, Del Mar, Calif.

[73] Assignee: Innercool Therapies, Inc., San Diego, Calif.

[21] Appl. No.: 09/028,567

[22] Filed: Feb. 24, 1998

[51] Int. Cl.⁷ .................. A61M 5/00; A61F 7/12
[52] U.S. Cl. .................................. 604/7; 604/113
[58] Field of Search ................. 604/19, 27, 93, 604/113, 114, 264, 523; 607/104, 105, 113

[56] References Cited

U.S. PATENT DOCUMENTS

| | | | |
|---|---|---|---|
| 3,298,371 | 1/1967 | Lee | 128/303.1 |
| 3,425,419 | 2/1969 | Dato | 128/400 |
| 3,971,383 | 7/1976 | van Gerven | 128/303.1 |
| 4,427,009 | 1/1984 | Wells et al. | 128/400 |
| 4,883,455 | 11/1989 | Leonard | 604/4 |
| 4,894,164 | 1/1990 | Polaschegg | 210/646 |
| 4,904,237 | 2/1990 | Janese | 604/28 |
| 5,024,668 | 6/1991 | Peters et al. | 606/194 |
| 5,147,355 | 9/1992 | Friedman et al. | 606/23 |
| 5,149,321 | 9/1992 | Klatz et al. | 604/52 |
| 5,150,706 | 9/1992 | Cox et al. | 128/400 |
| 5,190,539 | 3/1993 | Fletcher et al. | 606/25 |
| 5,211,631 | 5/1993 | Scheaff | 604/113 |
| 5,234,405 | 8/1993 | Klatz et al. | 604/24 |
| 5,257,977 | 11/1993 | Esbel | 604/113 |
| 5,269,749 | 12/1993 | Koturov | 604/4 |
| 5,269,758 | 12/1993 | Taheri | 604/96 |
| 5,281,215 | 1/1994 | Milder | 606/20 |
| 5,334,193 | 8/1994 | Nardella | 606/41 |
| 5,383,854 | 1/1995 | Safar et al. | 604/98 |
| 5,395,314 | 3/1995 | Klatz et al. | 604/24 |
| 5,403,281 | 4/1995 | O'Neill et al. | 604/113 |
| 5,423,807 | 6/1995 | Milder | 606/20 |
| 5,462,521 | 10/1995 | Brucker et al. | 604/20 |
| 5,486,204 | 1/1996 | Clifton | 607/96 |
| 5,486,208 | 1/1996 | Ginsburg | 607/106 |
| 5,558,644 | 9/1996 | Boyd et al. | 604/96 |
| 5,573,532 | 11/1996 | Chang et al. | 606/26 |
| 5,584,804 | 12/1996 | Klatz et al. | 604/24 |
| 5,624,392 | 4/1997 | Saab | 604/43 |
| 5,709,654 | 1/1998 | Klatz et al. | 604/24 |
| 5,807,391 | 9/1998 | Wijkamp | 606/23 |
| 5,820,593 | 10/1998 | Safar et al. | 604/96 |
| 5,827,222 | 10/1998 | Klatz et al. | 604/52 |
| 5,879,316 | 3/1999 | Safar et al. | 604/4 |
| 5,879,329 | 3/1999 | Ginsburg | 604/93 |
| 5,906,588 | 5/1999 | Safar et al. | 604/4 |

FOREIGN PATENT DOCUMENTS

| | | |
|---|---|---|
| 806 029 | 2/1981 | U.S.S.R. . |
| WO 98/26831 | 6/1998 | WIPO . |
| WO 98/31312 | 7/1998 | WIPO . |

OTHER PUBLICATIONS

Maas, C; Intermittent antegrade selective cerebral perfusion during circulatory arrest for repair of aortic arch; Perfusion, vol. 12, No. 2, pp. 127–132.

(List continued on next page.)

Primary Examiner—Ronald Stright
Assistant Examiner—Cheryl J. Huseman
Attorney, Agent, or Firm—Gerald W. Spinks

[57] ABSTRACT

A method and apparatus for performing hypothermia of a selected organ without significant effect on surrounding organs or other tissues, by perfusion of the organ with blood cooled externally from the body of the patient. A flexible supply catheter is inserted percutaneously into an artery. Blood from the supply catheter is cooled in a finned tube heat exchanger or a fluid bath. A flexible delivery catheter is inserted percutaneously through the vascular system of the patient to place the distal end of the catheter in an artery feeding the selected organ. An occlusion device is expanded to occlude the feeder artery at a point proximal to the distal end of the delivery catheter. Cooled blood from the chiller is pumped through the delivery catheter to an outlet near the distal end of the catheter, to cool the selected organ, distal to the tip of the delivery catheter.

22 Claims, 3 Drawing Sheets

OTHER PUBLICATIONS

Colvert, K; Opportunities with combined modality therapy for selective organ preservation in muscle–invasive bladder cancer, Journal of Surgical Oncology, vol. 63, No. 3, pp. 201–208, 1996.

Jansen, J.; Near Continuous Cardiac Output by Thermodilution ; Jun. 1996; Journal of Clinical Monitoring vol. 13; pp. 233–239.

Abstract of U. S. Pat. No. 4,427,009; Wells, et al.; Integrated Cardioplegia Delivery System ; Jan. 1984.

Abstract of U. S. Pat No. 4,894,164; Polaschegg; Apparatus for Treating Blood in an Extracorporeal Circuit ; Jan. 1990.

Abstract of U. S. Pat. No. 5,234,405; Klatz, et al.; Brain Resuscitation Device and Method for Performing the Same Aug. 1993.

Abstract of U. S. Pat. No. 5,558,644; Boyd, et al.; Retrograde Delivery Catheter and Method for Inducing Cardioplegic Arrest ; Sep. 1996.

Abstract of U. S. Pat. No. 5,584,804; Klatz, et al.; Brain Resuscitation and Organ Preservation Device and Method for Performing the Same ; Dec. 1996.

Marekovic, Z.; Abstract of Renal Hypothermia in Situ by Venous Passages : Experimental Work on Dogs ; European Urology 6(2); pp. 119–123; 1980.

Schwartz, A.; Isolated Cerebral Hypothermia by Single Carotid Artery Perfusion of Extracorporeally Cooled Blood in Baboons ; Neurosurgery, vol. 39, No. 3; pp. 577–582; Sep. 1996.

Abstract of U. S. Pat. No. 4,904,237; Janese; Apparatus for the Exchange of Cerebrospinal Fluid and a Method of Treating Brain and Spinal Cord Injuries ; Feb. 1990.

Abstract of U. S. Pat. No 5,149,321; Klatz; Brain Resuscitation Device and Method for Performing the Same ; Sep. 1992.

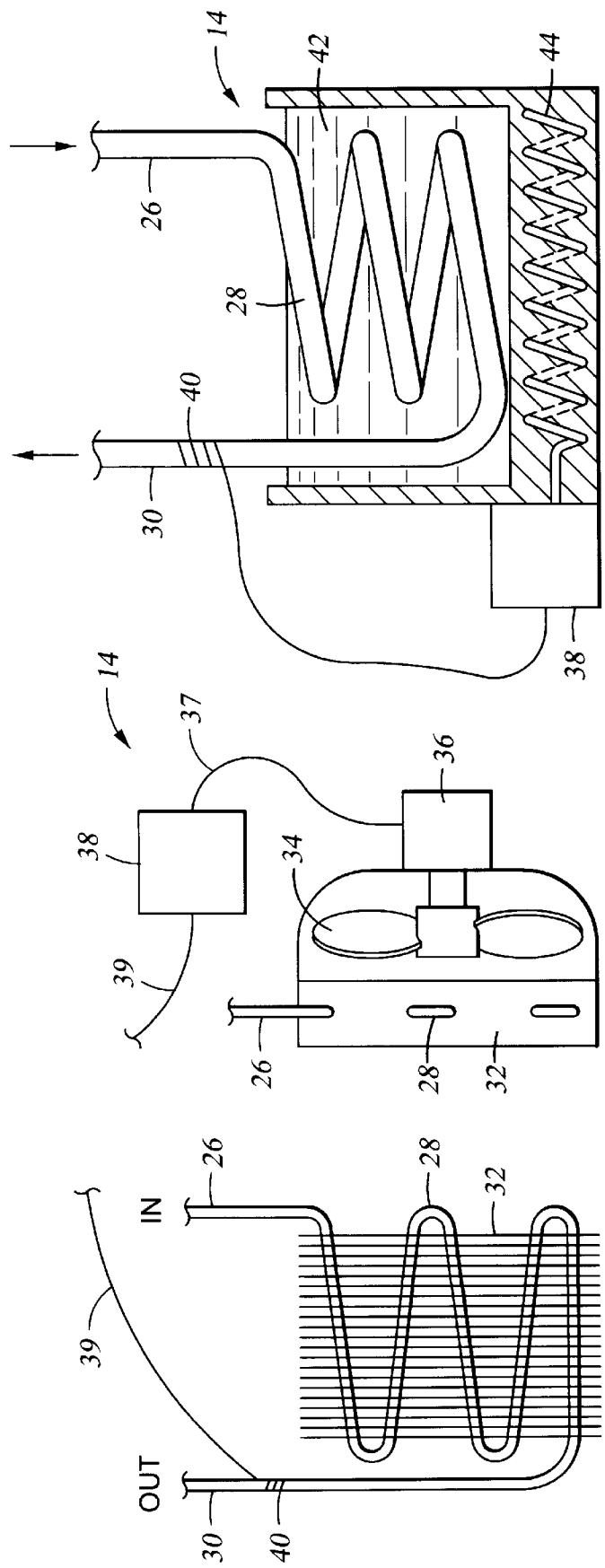

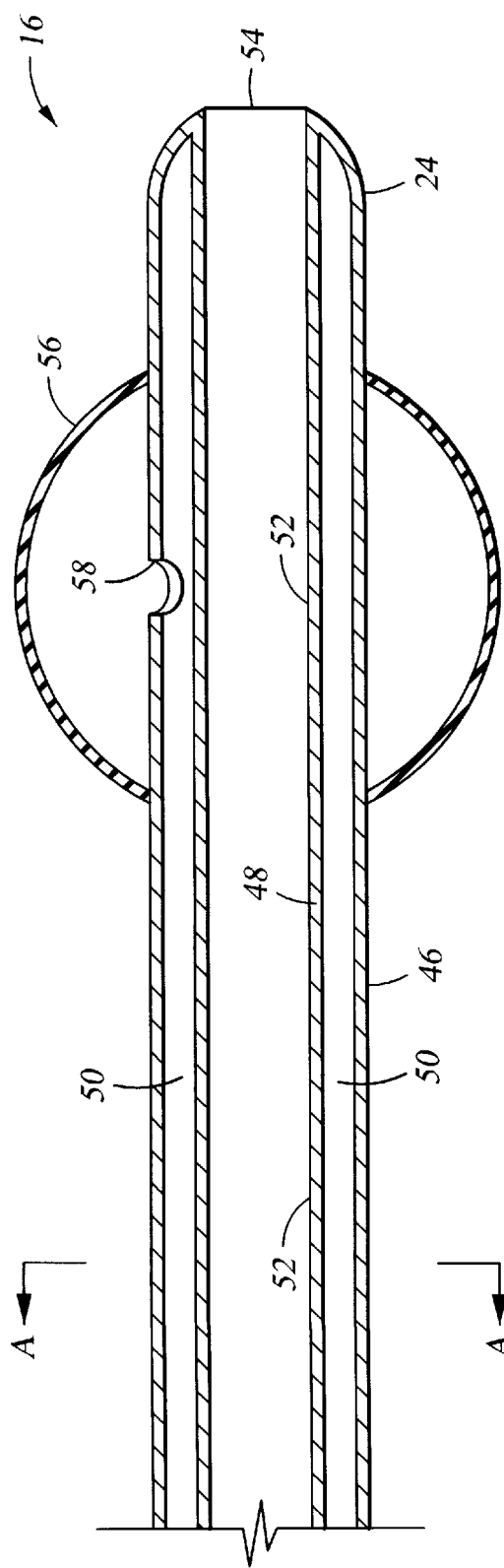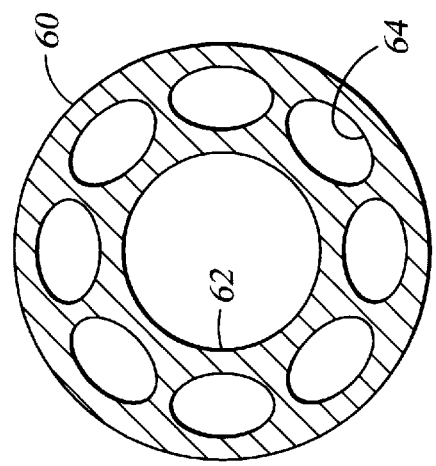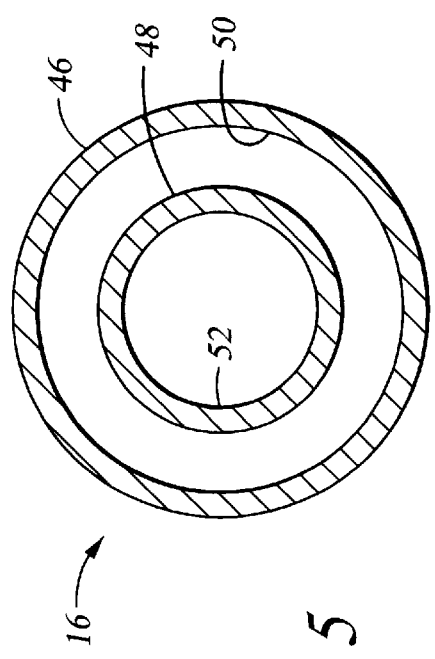
Fig. 4
Fig. 6
Fig. 5

INSULATED CATHETER FOR SELECTIVE ORGAN PERFUSION

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The current invention relates to selective cooling, or hypothermia, of an organ, such as the brain, by perfusing the organ with cooled blood. This cooling can protect the tissue from injury caused by anoxia or trauma.

2. Background Information

Organs of the human body, such as the brain, kidney, and heart, are maintained at a constant temperature of approximately 37° C. Cooling of organs below 35° C. is known to provide cellular protection from anoxic damage caused by a disruption of blood supply, or by trauma. Cooling can also reduce swelling associated with these injuries.

Hypothermia is currently utilized in medicine and is sometimes performed to protect the brain from injury. Cooling of the brain is generally accomplished through whole body cooling to create a condition of total body hypothermia in the range of 20° to 30° C. This cooling is accomplished by immersing the patient in ice, by using cooling blankets, or by cooling the blood flowing externally through a cardiopulmonary bypass machine. U.S. Pat. No. 3,425,419 to Dato and U.S. Pat. No. 5,486,208 to Ginsburg disclose catheters for cooling the blood to create total body hypothermia However, they rely on circulating a cold fluid to produce cooling. This is unsuitable for selective organ hypothermia, because cooling of the entire catheter by the cold fluid on its way to the organ would ultimately result in non-selective, or total body, cooling.

Total body hypothermia to provide organ protection has a number of drawbacks. First, it creates cardiovascular problems, such as cardiac arrhythmias, reduced cardiac output, and increased systemic vascular resistance. These side effects can result in organ damage. These side effects are believed to be caused reflexively in response to the reduction in core body temperature. Second, total body hypothermia is difficult to administer. Immersing a patient in ice water clearly has its associated problems. Placement on cardiopulmonary bypass requires surgical intervention and specialists to operate the machine, and it is associated with a number of complications including bleeding and volume overload. Third, the time required to reduce the body temperature and the organ temperature is prolonged. Minimizing the time between injury and the onset of cooling has been shown to produce better clinical outcomes.

Some physicians have immersed the patient's head in ice to provide brain cooling. There are also cooling helmets, or head gear, to perform the same. This approach suffers from the problems of slow cool down and poor temperature control due to the temperature gradient that must be established externally to internally. It has also been shown that complications associated with total body cooling, such as arrhythmia and decreased cardiac output, can also be caused by cooling of the face and head only.

Selective organ hypothermia has been studied by Schwartz, et. al. Utilizing baboons, blood was circulated and cooled externally from the body via the femoral artery and returned to the body through the carotid artery. This study showed that the brain could be selectively cooled to temperatures of 20° C. without reducing the temperature of the entire body. Subsequently, cardiovascular complications associated with total body hypothermia did not occur. Schwartz's method suffers from a significant disadvantage, however, in that the carotid artery must be cannulated. Percutaneous cannulation of the carotid artery is very difficult and potentially fatal, due to the associated arterial wall trauma. Such trauma could cause a stroke or excessive blood loss. This situation is exacerbated by the fact that the catheter must be left in place for an extended period of time. Further, because of the deep location of the carotid artery in the neck, a multitude of vital structures, such as cranial nerves, the thyroid gland, and the jugular vein must be passed safely. Also, this method could not be used to cool organs such as the kidneys, where the renal arteries cannot be directly cannulated percutaneously.

Selective organ hypothermia has also been attempted by perfusing the organ with a cold solution, such as saline or perflourocarbons. This is commonly done to protect the heart during heart surgery, and is referred to as cardioplegia. This procedure has a number of drawbacks, including limited time of administration due to excessive volume accumulation, cost and inconvenience of maintaining the perfusate, and lack of effectiveness due to temperature dilution from the blood. Temperature dilution by the blood is a particular problem in high blood flow organs such as the brain. For cardioplegia, the blood flow to the heart is minimized; therefore, temperature dilution is minimized.

BRIEF SUMMARY OF THE INVENTION

Percutaneous catheterization through a femoral artery, to perform selective organ perfusion with cooled blood from the patient, is the ideal method of achieving selective organ hypothermia. First, because only the target organ is cooled, complications associated with total body hypothermia are avoided. Second, both supply and return punctures, and arterial vessel cannulations, can be performed at easily accessible arteries such as the femoral or brachial. Third, cold perfusate solutions are not required, thus eliminating problems with excessive fluid accumulation. This also eliminates the time, cost, and handling issues associated with providing and maintaining cold perfusate solution. Fourth, rapid cooling can be achieved. Fifth, precise temperature control is possible.

Problems associated with inserting a catheter into a blood vessel wall can be minimized by cannulation of the femoral or brachial arteries. These arteries are more superficial than the carotid artery, for instance, and do not have the numerous vital structures surrounding them. Further, they do not supply blood directly to the brain or other vital organs, but rather to the extremities, which are more tolerant of decreased blood flow, or loss of blood flow. However, these arteries are remote from organs. For example, to reach the brain, a catheter placed in the femoral artery would have to pass 70 to 100 cm through the iliac artery and the aorta. Use of a standard single wall catheter would result in warming of the cooled blood on the way to the organ, such that selective hypothermia of the organ could not be achieved.

This problem of blood warming is overcome in the present invention by using a thermally insulated delivery catheter. Such a catheter would have a layer of insulation between the lumen carrying the chilled blood and the external blood in the conduit arteries. Thus, blood could be withdrawn from the femoral artery with a standard catheter, chilled externally, and delivered via the other femoral artery to the brain, with the insulated delivery catheter.

The selective organ cooling achieved by the present invention is accomplished by placing a thermally insulated delivery catheter into the feeding artery of the selected organ. A blood supply, drawn from a remote artery with a standard catheter, is cooled external to the body and then delivered to the selected organ through the insulated delivery catheter. In one embodiment, the insulated delivery catheter would have a coaxial construction. The inner tube of the delivery catheter would serve as the blood carrying lumen. The annular gap between the inner and outer tubes would be sealed at the distal end, near the port where the cooled blood exits from the inner tube. The annular gap could be evacuated to provide an insulation barrier against heat transfer into the inner tube. This vacuum could be performed actively, in that a vacuum pump or syringe could be connected to the proximal portion of the annular gap, to pull a vacuum during use of the delivery catheter. Alternatively, the proximal portion of the annular gap could be sealed after a vacuum is pulled, resulting in a passive vacuum.

The annular gap could also be filled with insulating material. Room air could be such a material. Alternatively, an insulating foam or gel could fill the annular gap. Aerogel or polyurethane foams could suffice.

In another embodiment, a single wall catheter could be constructed with a ring of parallel longitudinal lumens in the wall of the catheter, surrounding an inner lumen for blood flow. These outer longitudinal lumens could be evacuated, actively or passively, or filled with insulating material, similarly to the annular gap.

Any of these catheter embodiments could have a selectively inflatable and deflatable balloon near the distal end of the delivery catheter, to occlude the feeder artery in which the catheter is placed. This would be important to prevent thermal dilution of the cooled delivered blood by the warm blood normally flowing in the feeder artery. The blood delivered by the catheter would serve to oxygenate and supply nutrients to the organ being cooled.

The supply and delivery catheters would be attached to the inlet and outlet, respectively, of a blood chiller. This apparatus would cool the blood outside the body to the desired temperature. Such an apparatus could be an ambient air heat exchanger in which finned stainless steel tubes would carry blood and exchange heat with the environment. A fan could be used to blow ambient air across the fins. Alternatively, a coil of stainless steel tubes could be placed in a water bath. The water bath temperature could be controlled to the desired temperature by heating or cooling. The water bath would remove heat from the blood in the coil.

Depending upon the size of the arteries through which the delivery catheter must pass, and depending upon the pressure required to deliver the blood to the selected organ, it may be necessary to incorporate a pump in the apparatus, to deliver the blood to the organ. Such a pump could be of the peristaltic variety or of the diaphragm or piston variety. These pumps could provide the pulsatile flow which naturally occurs in the feeder arteries of organs. Alternatively, if arterial space is available, a catheter with a large blood delivery lumen could be used, so that the natural arterial pressure created by the heart in the supply artery could deliver the cooled blood to the organ.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 2A is a front elevation view of a finned tube heat exchanger for use in the chiller of the apparatus shown in FIG. 1;

FIG. 2B is a side elevation view of the finned tube heat exchanger shown in FIG. 2;

FIG. 3 is a schematic view of a fluid bath heat exchanger for use in the chiller of the apparatus shown in FIG. 1;

FIG. 4 is a longitudinal section view of the distal end of the delivery catheter shown in FIG. 1;

FIG. 5 is a transverse section view of a first embodiment of the delivery catheter shown in FIG. 4, taken at the line A—A; and FIG. 6 is a transverse section view of a second embodiment of the delivery catheter shown in FIG. 4.

DETAILED DESCRIPTION OF THE INVENTION

Figure 1:
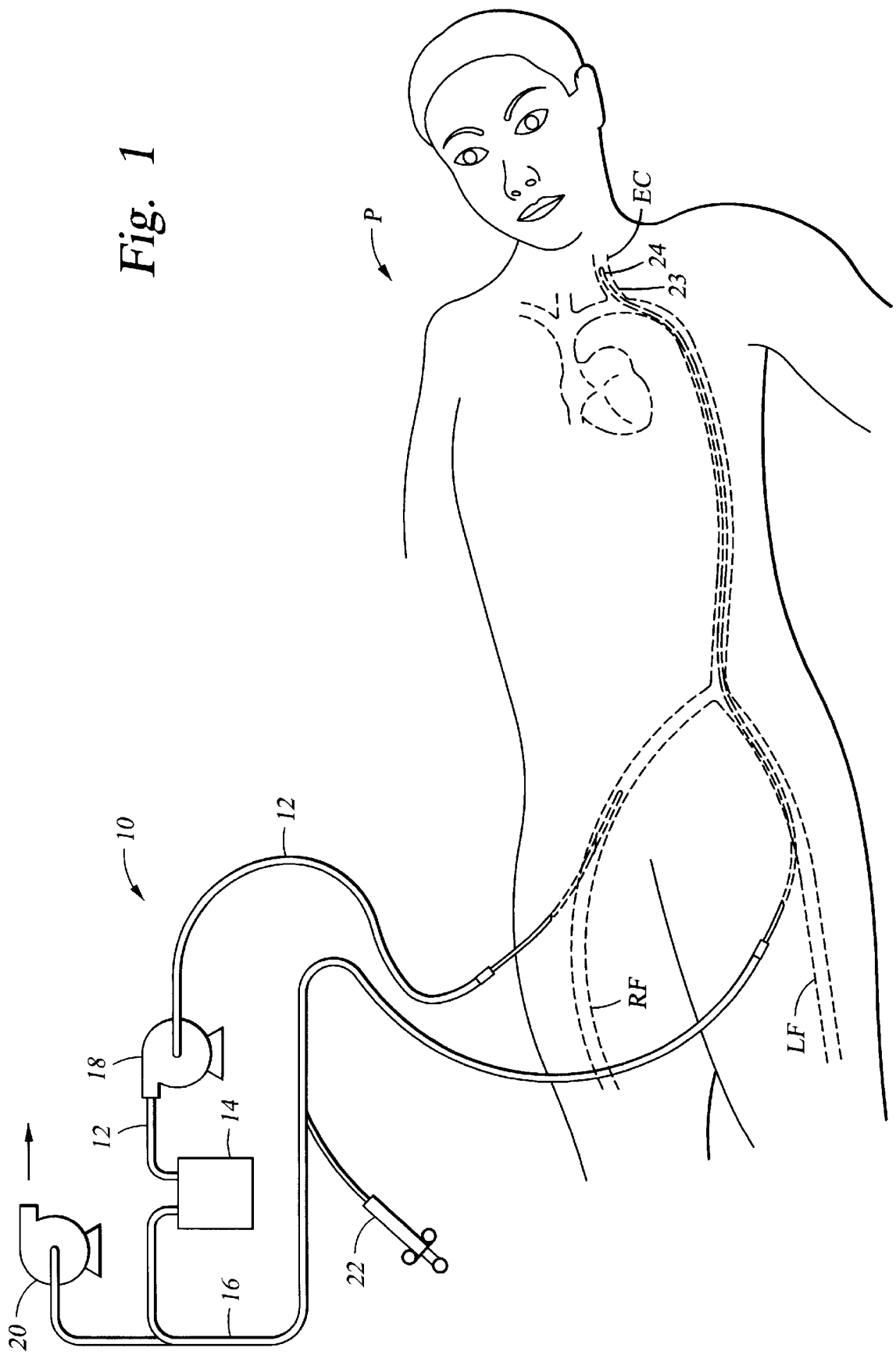
FIG. 1 is a schematic view of the apparatus of the present invention in use to cool the brain of a patient.

As shown in FIG. 1, the selective organ hypothermia apparatus 10 of the present invention includes a supply catheter 12, a chiller 14, and a delivery catheter 16. The supply catheter 12 is a single wall flexible catheter having a diameter sufficiently small to allow its distal end to be inserted percutaneously into an accessible artery such as the right femoral artery RF of a patient P. Blood from the right femoral artery RF flows through the supply catheter 12 to the chiller 14, where the blood is chilled to a selected temperature below the body temperature of the patient P. The cooled blood exits the chiller 14 into the delivery catheter 16, which is a flexible insulated catheter. The insulated delivery catheter 16 has a diameter sufficiently small to allow the delivery catheter 16 to be inserted percutaneously into an accessible artery such as the left femoral artery LF of the patient P. The diameter of the delivery catheter 16 is sufficiently small, and the delivery catheter 16 is sufficiently long, to allow the distal end 24 of the delivery catheter 16 to be passed through the vascular system of the patient P and placed in the external carotid artery EC. The cooled blood flows through the insulated delivery catheter 16 to exit near the distal end 24 of the delivery catheter 16, to selectively achieve hypothermia of the brain, by perfusion.

The hypothermia apparatus 10 of the present invention may also include a pump 18, which is connected into the supply catheter 12, with its suction port being connected in fluid flow communication with the artery, and its discharge port being connected in fluid flow communication with the inlet of the chiller 14. The pump 18 is used in situations in which the allowable diameter of the delivery catheter 16 is so small that the normal arterial pressure feeding the supply catheter 12 is not sufficient to cause an adequate amount of blood to flow through the apparatus to the distal end 24 of the delivery catheter 16.

The hypothermia apparatus 10 of the present invention may also include a vacuum source, such as a vacuum pump 20, to actively evacuate and maintain the vacuum in an insulating layer within the delivery catheter 16. Another type of vacuum source, such as a syringe (not shown), could also be used instead of the vacuum pump 20. Finally, the hypothermia apparatus 10 of the present invention may also include an occlusion device, such as an inflatable balloon 23, near the distal end 24 of the delivery catheter 16. If the occlusion device is an inflatable balloon 23, the apparatus will also include a pressure source, such as a syringe 22, for inflating the balloon 23. The occlusion device could also take other forms, such as, for example, a self-expanding bulb which can be released by withdrawing a retaining sheath, without departing from the spirit of the present invention. The purpose of the occlusion device is to occlude the feeder artery of the selected organ, to prevent the cooled blood from being thermally diluted by warm blood flowing through the feeder artery.

FIG. 2A shows a first embodiment of the cooling mechanism which may be used in the chiller 14. In this embodiment, the proximal end of the supply catheter 12 is connected to the inlet 26 of a stainless steel tube 28, which makes several passes through a finned tube heat exchanger 32. The outlet 30 of the stainless steel tube 28 is connected to the proximal end of the insulated delivery catheter 16. A temperature sensor, such as a thermocouple 40, is attached to the outlet 30 of the heat exchanger 32, for use in controlling the temperature of the cooled blood. FIG. 2B shows a side view of the heat exchanger 32, illustrating how a fan 34 can be used to blow ambient air through the heat exchanger 32. The fan 34 is driven by a motor 36, which is connected by a cable 37 to a temperature controller 38. The temperature controller 38 is connected by a second cable 39 to the thermocouple 40.

FIG. 3 shows a second embodiment of the cooling mechanism which may be used in the chiller 14. In this embodiment, the proximal end of the supply catheter 12 is again connected to the inlet 26 of a stainless steel tube 28, which is coiled within a fluid bath 42. Here as before, the outlet 30 of the stainless steel tube 28 is connected to the proximal end of the insulated delivery catheter 16. A temperature sensor, such as a thermocouple 40, is attached to the outlet 30 of the coiled stainless steel tube 28, for use in controlling the temperature of the cooled blood. A temperature controller 38 is connected to the thermocouple 40, and to a heating and/or cooling element 44. Depending upon the desired temperature of the cooled blood, it may be necessary to heat or cool the fluid in the fluid bath 42. Sufficient heat may escape from the fluid bath 42 to the environment to require the application of heat with the temperature control element 44, in which case the temperature control element 44 could be a resistive heating element. On the other hand, in some applications and some environments, it may be necessary to apply cooling to the fluid bath 42 with the temperature control element 44, in which case the temperature control element 44 could be a liquid cooled coil.

FIG. 4 is a longitudinal section view of the distal end 24 of one embodiment of the insulated delivery catheter 16. This embodiment of the delivery catheter 16 has a coaxial construction, with an outer tube 46 and an inner tube 48. An annular insulating gap 50 is created between the outer tube 46 and the inner tube 48. The annular insulating gap 50 can be evacuated during manufacture of the delivery catheter 16. If evacuated during manufacture, the annular insulating gap 50 could be sealed at its proximal end, creating a constant, passive vacuum in the insulating gap 50. Alternatively, the annular insulating gap 50 could be evacuated during use of the delivery catheter 16, such as by the vacuum pump 20 discussed above, or by a syringe (not shown). Conversely, the annular insulating gap 50 could be filled with an insulating material. Examples of suitable insulating materials are air, insulating foam such as polyurethane, or aerogel. An inner lumen 52 for the cooled blood flow is formed within the inner tube 48, with an exit port 54 adjacent the distal end 24 of the delivery catheter 16.

Since it will normally be beneficial to prevent thermal dilution of the cooled blood flow, the distal end 24 of the delivery catheter 16 can be provided with a selectively expandable and retractable occlusion device such as an inflatable balloon 56. The balloon 56 can be an expandable membrane sized to inflate to a size sufficient to occlude the feeder artery in which the delivery catheter distal end 24 is placed. Known technology could be used to manufacture the balloon 56 of a material which will expand only to a desired maximum size, which would be designed to occlude the feeder artery, without expanding further. Air, or another suitable fluid, can be provided to inflate the balloon 56 via an inflation port 58 in the outer tube 46 of the delivery catheter 16. If air, for example, is used to fill the annular insulating gap 50, this air can also be pressurized to inflate the balloon 56, with pressure being selectively provided by the syringe 22. If, on the other hand, the annular insulating gap 50 is evacuated, inflation air would have to be provided to the balloon 56 by an inflation duct (not shown), which could pass from the syringe 22 through the annular gap 50 to the inflation port 58. Similarly, if the annular insulating gap 50 is filled with another insulating material such as foam, inflation air would have to be provided to the balloon 56 by an inflation duct (not shown), which could pass from the syringe 22 through the annular gap 50 to the inflation port 58.

FIG. 5 is a transverse section of the embodiment of the insulated delivery catheter 16 shown in FIG. 4. This Figure clearly shows the arrangement of the outer tube 46, the inner tube 48, the insulating annular gap 50, and the blood lumen 52.

FIG. 6 is a transverse section of a second embodiment of the insulated delivery catheter 16. It should be noted that a longitudinal section of this second embodiment would have the same appearance as the longitudinal section of the first embodiment, shown in FIG. 4. In this second embodiment, the delivery catheter 16 has a single wall 60, with an inner lumen 62 for flow of the cooled blood. A plurality of longitudinal outer insulating lumens 64 are arranged surrounding, and parallel to, the inner lumen 62. Each outer insulating lumen 64 can be evacuated during manufacture of the delivery catheter 16. If evacuated during manufacture, each of the outer insulating lumens 64 could be sealed at its proximal end, creating a constant, passive vacuum in each of the outer insulating lumens 64. Alternatively, the outer insulating lumens 64 could be evacuated during use of the delivery catheter 16, such as by the vacuum pump 20 discussed above, or by a syringe (not shown). Conversely, the outer insulating lumens 64 could be filled with an insulating material.

In this second embodiment, air, or another suitable fluid, can be provided to inflate the balloon 56 via an inflation port 58 from one or more of the outer insulating lumens 64 through the outer surface of the delivery catheter 16. If air, for example, is used to fill the outer insulating lumens 64, this air can also be pressurized to inflate the balloon 56, with pressure being selectively provided by the syringe 22. If, on the other hand, the outer insulating lumens 64 are evacuated, inflation air would have to be provided to the balloon 56 by one or more inflation ducts (not shown), which could pass from the syringe 22 through one or more of the outer insulating lumens 64 to one or more inflation ports 58. Similarly, if the outer insulating lumens 64 are filled with another insulating material such as foam, inflation air would have to be provided to the balloon 56 by one or more inflation ducts (not shown), which could pass from the syringe 22 through one or more of the outer insulating lumens 64 to one or more inflation ports 58.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. An apparatus for selective organ hypothermia by perfusion, said apparatus comprising:
    a chiller;
    a flexible elongated supply catheter, said supply catheter having a proximal end attachable to an inlet of said chiller, said supply catheter having a distal end percutaneously insertable into an artery of a patient;
    a flexible elongated delivery catheter, said delivery catheter having a proximal end attachable to an outlet of said chiller, said delivery catheter having sufficient length and sufficiently small diameter to be insertable percutaneously through a vascular system of a patient to a feeder artery of a selected organ of a patient, said delivery catheter having a lumen for flow of cooled blood from said chiller to a feeder artery of a selected organ of a patient;
    an insulating layer in said delivery catheter between said blood lumen and the outer surface of said delivery catheter; and
    a blood outlet formed in said blood lumen, near a distal end of said delivery catheter.

2. An apparatus as recited in claim 1, wherein said insulating layer comprises an annular space surrounding said blood lumen.

3. An apparatus as recited in claim 2, wherein said annular space contains a vacuum.

4. An apparatus as recited in claim 3, further comprising a vacuum device connected to said annular space for actively maintaining said vacuum.

5. An apparatus as recited in claim 2, wherein said annular space contains a material of low thermal conductivity.

6. An apparatus as recited in claim 1, wherein said insulating layer comprises a plurality of longitudinal channels in a wall of said delivery catheter, said longitudinal channels being arranged parallel to, and surrounding, said blood lumen.

7. An apparatus as recited in claim 6, wherein each said longitudinal channel contains a vacuum.

8. An apparatus as recited in claim 7, further comprising a vacuum device connected to said plurality of longitudinal channels for actively maintaining said vacuum.

9. An apparatus as recited in claim 6, wherein each said longitudinal channel contains a material of low thermal conductivity.

10. An apparatus as recited in claim 1, further comprising an occlusion device adjacent said distal end of said delivery catheter, said occlusion device being selectively expandable to occlude the feeder artery of the selected organ, at a point proximal to said blood outlet.

11. An apparatus as recited in claim 10, wherein said occlusion device comprises a selectively expandable and retractable membrane mounted on said delivery catheter.

12. An apparatus as recited in claim 11, wherein said expandable membrane comprises a selectively inflatable and deflatable balloon.

13. An apparatus as recited in claim 1, further comprising a pump connected to said supply catheter to pump blood through said supply catheter, said chiller, and said delivery catheter.

14. An apparatus as recited in claim 1, wherein said chiller comprises a finned tube heat exchanger.

15. An apparatus as recited in claim 1, wherein said chiller comprises a coil immersed in a fluid bath.

16. An apparatus for selective organ hypothermia by perfusion, said apparatus comprising:
    a chiller;
    a flexible elongated supply catheter, said supply catheter having a proximal end connected in fluid flow communication with an inlet of said chiller, said supply catheter having a distal end percutaneously insertable into an artery of a patient;
    a pump connected to said supply catheter;
    a flexible elongated delivery catheter, said delivery catheter having a proximal end connected in fluid flow communication with an outlet of said chiller, said delivery catheter having sufficient length and sufficiently small diameter to be insertable percutaneously through a vascular system of a patient to a feeder artery of a selected organ of a patient, said delivery catheter having a lumen for flow of cooled blood from said chiller to a feeder artery of a selected organ of a patient;
    an insulating layer in said delivery catheter between said blood lumen and the outer surface of said delivery catheter;
    a blood outlet formed in said blood lumen, near a distal end of said delivery catheter; and
    an occlusion device formed on said distal end of said delivery catheter, said occlusion device being selectively expandable to occlude the feeder artery of the selected organ, at a point proximal to said blood outlet.

17. A method for selective organ hypothermia by perfusion, said method comprising:
    providing a chiller, a flexible supply catheter connected to an inlet of said chiller, and a flexible delivery catheter connected to an outlet of said chiller, said delivery catheter having a blood lumen, an insulating layer around said lumen, and a blood outlet adjacent its distal end;
    percutaneously inserting a distal end of said supply catheter into an artery of a patient;
    percutaneously inserting a distal end of said delivery catheter into an easily accessible artery near the skin of the patient;
    passing said delivery catheter through the vascular system of the patient to place said distal end of said delivery catheter in a feeder artery of a selected organ;
    flowing blood from the supply artery through said supply catheter, said chiller, and said delivery catheter, to the feeder artery of the selected organ; and
    cooling blood flowing through said chiller, and maintaining the blood flow in said delivery catheter at a lowered temperature, to enable said blood to flow distally into the selected organ and cool the organ.

18. A method as recited in claim 17, further comprising providing a pump attached to said supply catheter, and wherein said flowing of blood comprises pumping of blood from the supply artery through said supply catheter, said chiller, and said delivery catheter, to the feeder artery of the selected organ.

19. A method as recited in claim 17, further comprising:

providing an occlusion device adjacent said distal end of said delivery catheter at a point proximal to said blood outlet; and selectively expanding said occlusion device to occlude the feeder artery of the selected organ.

20. A method for selective organ hypothermia by perfusion, said method comprising:

providing a supply catheter and a flexible insulated delivery catheter;

introducing a distal end of said supply catheter into an artery of a patient;

introducing said insulated catheter into the vascular system of a patient to place a distal end of said insulated catheter in a feeding artery of an organ of the patient;

withdrawing blood from said patient through said supply catheter;

cooling said blood in a chiller;

delivering said cooled blood to said feeding artery via said insulated delivery catheter; and cooling said organ by flow of said cooled blood through said feeding artery.

21. A method for selective brain hypothermia by perfusion, said method comprising:

providing a supply catheter and a flexible insulated delivery catheter;

introducing a distal end of said supply catheter into an artery of a patient;

introducing said insulated catheter into the vascular system of a patient to place a distal end of said insulated catheter in a carotid artery of the patient;

withdrawing blood from said patient through said supply catheter;

cooling said blood in a chiller;

delivering said cooled blood to said carotid artery via said insulated delivery catheter; and cooling the brain of the patient by flow of said cooled blood through said carotid artery.

22. A method for selective hypothermia of the heart of a patient, by perfusion, said method comprising:

providing a supply catheter and a flexible insulated delivery catheter;

introducing a distal end of said supply catheter into an artery of a patient;

introducing said insulated catheter into the vascular system of a patient to place a distal end of said insulated catheter in a feeding artery of the heart of the patient;

withdrawing blood from said patient through said supply catheter;

cooling said blood in a chiller;

delivering said cooled blood to said feeding artery via said insulated delivery catheter; and cooling the heart of the patient by flow of said cooled blood through said feeding artery.

* * * * *